(12) United States Patent
Tatsuki et al.

(10) Patent No.: US 8,278,360 B2
(45) Date of Patent: Oct. 2, 2012

(54) BEHAVIOR-DISRUPTING AGENT AND BEHAVIOR-DISRUPTING METHOD OF ARGENTINE ANT

(75) Inventors: Sadahiro Tatsuki, Tokyo (JP); Mamoru Terayama, Tokyo (JP); Yasutoshi Tanaka, Tokyo (JP); Takehiko Fukumoto, Joetsu (JP)

(73) Assignee: Shin-Etsu Chemical Co., Ltd., Chiyoda-ku, Tokyo (JP)

( * ) Notice: Subject to any disclaimer, the term of this patent is extended or adjusted under 35 U.S.C. 154(b) by 1061 days.

(21) Appl. No.: 11/063,900

(22) Filed: Feb. 23, 2005

(65) Prior Publication Data
US 2005/0209344 A1 Sep. 22, 2005

(30) Foreign Application Priority Data

Mar. 17, 2004 (JP) ................. 2004-075436

(51) Int. Cl.
*A01N 35/00* (2006.01)
*A01N 35/02* (2006.01)
*A01N 35/04* (2006.01)
(52) U.S. Cl. ....................................................... 514/703
(58) Field of Classification Search .................. 514/703
See application file for complete search history.

(56) References Cited

U.S. PATENT DOCUMENTS 5,925,367 A * 7/1999 Angst et al. ................ 424/405
6,395,776 B1 * 5/2002 Losel et al. ................ 514/531

OTHER PUBLICATIONS

Cavill et al., Experientia 35,1979, Birkhauser Veriag Basel, p. 989-990.*
Van Vorhis Key et al., Journal of Chemical Ecology, 1982, vol. 8, No. 7,pp. 1057-1063.*
Klotz et al., Journal of Agriculture and Urban Entomology,2002, vol. 19, No. 2, pp. 85-94.*
G.W.K. Cavill, N. W. Davies, and F.J. McDonald, Characterization of Aggregation Factors and Associated Compounds From the Argentine Ant, Journal of Chemical Ecology, vol. 6, pp. 371-384 (1980).
Japanese Office Action for Japanese Application No. 2004-075436.
Greenberg et al., "Argentine Ant (Hymenoptera: Formicidae) Trail Pheromone Enhances Consumption of Liquid Sucrose Solution", *Entomological Society of America*, 2000, vol. 93, No. 1, pp. 119-122.
Key et al., "Trail Pheromone-Conditioned Anemotaxis by the Argentine Ant, *Iridomyrmex humilis*", *Ent. Exp. & appl.*, vol. 32, No. 3 (1982), pp. 232-237.
Yamaoka, "Ant Trail Pheromone and Use Thereof in Movie Directed by Kurosawa", Kouryo by Japan Perfumery & Flavoring Association, Sep. 30, 1992, No. 175, pp. 41-47.

* cited by examiner

*Primary Examiner* — Fereydoun G Sajjadi
*Assistant Examiner* — Courtney Brown
(74) *Attorney, Agent, or Firm* — Alston & Bird LLP

(57) ABSTRACT

Provided are a behavior-disrupting agent of Argentine ants for controlling them or suppressing their reproduction is a safer and more effective manner, and the behavior-disrupting method of them. More specifically, a behavior-disrupting agent of Argentine ants comprising Z-9-hexadecenal, and a behavior-disrupting method of Argentine ants comprising a step of using the behavior-disrupting agent are provided based on the finding that the behavior of Argentine ants is disrupted by emission of Z-9-hexadecenal, which is a trail pheromone, into the atmosphere.

7 Claims, No Drawings

BEHAVIOR-DISRUPTING AGENT AND BEHAVIOR-DISRUPTING METHOD OF ARGENTINE ANT

BACKGROUND OF THE INVENTION

1. Field of the Invention

The present invention relates to a behavior-disrupting agent and a behavior-disrupting method of the Argentine ant scientific name: *Linepithema humile*).

2. Description of the Related Art

The Argentine ant (*Linepithema humile*) is, as its name suggests, the ant coming from South American countries such as Argentine. Its distribution is spreading to North America, Europe, Africa and Australia owing to the human activities and circulation of commodities accompanying, for example, trade. The Argentine ant is a difficult-to-control insect whose problems such as damage to agricultural crops, invasion into houses as a noxious ant and expulsion of endemic ant species causing deterioration in the ecosystem have recently become apparent in Japan.

Invasion to Asian countries were not known until the recent years. In 1993, the inhabitation of the Argentine ants was confirmed for the first time in Hiroshima Prefecture. Since then, they have been discovered in Yamaguchi Prefecture and Hyogo Prefecture. They are active at a temperature range of from 5 to 35° C. so that their distribution may spread mainly on the Pacific side of the western Japan and eastern Japan. The main problem in Japan at present is that they invade into houses as noxious ants. Owing to their strong reproductive power and active behavioral characteristics, expulsion of endemic ant species has been observed in their hot spot and they have already had an adverse effect on the ecosystem. In future, there is a fear of their causing damage to agricultural crops which have already been a problem overseas.

Insecticides or toxic baits are used for controlling Argentine ants because they have a high reproductive power and their active area is wide. In addition to their insufficient effects, frequent use of insecticides has a bad influence on human bodies and moreover, it may destruct the balance of ecosystem including the relationship with natural enemies. There is accordingly an eager demand for the development of a safe controlling method of them.

It should be noted that the main component of a trail pheromone of Argentine ants was identified as Z-9-hexadecenal about 20 years ago (see Cavill, G. W. K., N. W. Davies, and F. J. McDonald (1980) J. Chem. Ecol., 6, 371-384.)

SUMMARY OF THE INVENTION

With the foregoing in view, the present invention has been completed. An object of the present invention is to provide a behavior-disrupting agent and behavior-disrupting method of the Argentine ant to control it or prevent its reproduction safely and effectively as much as possible.

The present inventors have carried out an extensive investigation in order to attain the above-described object. As a result, it has been found that the behavior of Argentine ant can be disturbed by emitting Z-9-hexadecenal, which is a trail pheromone, into the atmosphere, leading to the completion of the invention.

In the present invention, there are thus provided a behavior-disrupting agent of the Argentine ant comprising z-9-hexadecenal, and a behavior-disrupting method of the Argentine ant comprising a step of using the behavior-disrupting agent.

Use of the behavior-disrupting agent according to the present invention makes it possible to disturb the marching and foraging behaviors of the Argentine ant, thereby safely and effectively controlling the Argentine ant which has hitherto been controlled only by the use of insecticides or toxic baits.

DETAILED DESCRIPTION OF THE PREFERRED EMBODIMENTS

The Z-9-hexadecenal to be used in the invention is a trail pheromone which is a chemical substance secreted by worker ants and laid by them on a route from their nest toward a food source to enable the other worker ants to follow the trail right to the food. As described above, the trail pheromone of Argentine ants has already been identified as Z-9-hexadecenal.

When Z-9-hexadecenal obtained by synthesis is emitted at a high concentration on or above the ground where Argentine ants live, it effectively disturbs passing the information on a food source among worker ants, thereby disrupting their behavior.

It is conventionally known that emission of synthetic pheromone to pest insects belonging to *Lepidoptera* such as moths at a high concentration disrupts their communication effectively. On the other hand, social insects such as ants and termites have the habit of laying a trail to their colony (nest) with their secretion, whereby they can return to the colony without fail. This secretion is a trail pheromone. The behavior disruption caused by emission of this trail pheromone in a large amount is however not known at all.

The Z-9-hexadecenal to be used in the invention, which will hereinafter be abbreviated as "Z-9-HDAL", is a synthetic trail pheromone of Argentine ants. It can be synthesized in a known manner. For example, it is commonly prepared by oxidizing desirable primary alcohol into aldehyde by an various oxidizer (see "Synthesis and Reaction of organic Compounds {II}" of New Experimental Chemistry Course 14, edited by the Chemical Society of Japan and published by Maruzen, page 636) or by hydrolyzing acetal produced by the reaction between a Grignard reagent and alkyl orthoformate into aldehyde and an alcohol (see Smith and Nicohols, J. Org. Chem., 6, 489(1941)).

The behavior-disrupting agent according to the invention may preferably comprise from 80 to 95 wt % of Z-9-HDAL. The Z-9-HDAL may be preferably as pure as possible. The content of its geometric isomer may be preferably 10 wt % or less.

The behavior-disrupting agent according to the invention may comprise, in addition to the above-described component, an antioxidant such as butylhydroxytoluene, butylhydroxyanisole, hydroquinone or Vitamin E and an ultraviolet absorber such as 2-hydroxy-4-octoxybenzophenone. The content of the antioxidant may be typically from 0.1 to 10 wt %, while that of the ultraviolet absorber may be typically from 0.01 to 10 wt %.

In the behavior-disrupting method according to the invention, in order to continue the effect of the Z-9-HDAL contained as an effective ingredient for a long period of time, the behavior-disrupting agent may be filled in a plastic vessel which can control a release amount, wherein the vessel may include a fine tube, a laminate bag and an ampoule and the plastic may include polyethylene, polypropylene and ethylene-vinyl acetate copolymer. Alternately, a rubber cap dipped in the agent may be used.

The amount of the Z-9-HDAL may be preferably from 10 to 500 mg per preparation. Particularly in the case of Argentine ants, a preparation excellent in strained release can be obtained by using a high density polyethylene tube. The reparations may be preferably placed at from 25 to 250 points per 100 m².

The embodiments of the present invention will next be described on basis of examples and comparative examples. It should not be construed that the present invention is limited to or by them.

PREPARATION OF A BEHAVIOR DISRUPTING AGENT

The Z-9-HDAL (purity: 92.0%) was dissolved in a mixture of 2 wt % of DBH (2,5-di-tert-butylhydroquinone) as an antioxidant and 2 wt % of 2-(2'-hydroxy-3'-tert-butyl-5'-methylphenyl)-5-chlorobenzotriazole as an ultraviolet absorber to form a solution. About 80 mg of the solution was filled in a high-density polyethylene hollow tube of 20 cm long and then the filled tube was hermetically sealed at both ends of the tube. Thus, a behavior-disrupting-agent was prepared.

EXAMPLE 1

The above behavior-disrupting agents were placed in the middle of marching of Argentine ants in a residential area in Iwakuni city of Yamaguchi Prefecture. Just after that, the marching behaviors were disturbed and their marching was stopped. It was observed that the Argentine ants ran about in confusion and they stopped their active movement, stayed around there and seemed as if they are detained.

EXAMPLE 2

The above behavior-disrupting agents of Argentine ants were placed in residential areas where the heavy breeding of Argentine ants was observed, on the branches or trunks of garden trees where many aphids and scales as well as ants were observed, and in cracks of concrete walls where marching of ants were observed. The number of ants, state of their marching and the number of nest inlets were then studied. As a result, the nests still existed, but the marching of ants decreased and the numbers of nest inlets and of ants remarkably decreased. Particularly, around crops near the nest inlets, the number of ants drastically decreased owing to the treatment with the behavior-disrupting agent.

EXAMPLE 3

In three plots in Iwakuni City of Yamaguchi Prefecture (control plot: 54 m², treated plot A: 80 m², treated plot B: 100 m²), poles were placed at almost regular intervals and the behavior-disrupting agents were attached to the poles at the height of 40 cm from the ground. The number of poles on which the agents were placed was zero in the control plot, 184 in the treated plot A and 221 in the treated plot B.

As a bait, paper dishes to which a honeybee solution had been added dropwise were placed in each plot at a portion of one paper dish per 4 m² on the day before placement of the behavior-disrupting agents, one hour after the placement, the day before removal of the agents (22 days after the placement), one hour after the removal, and two hours after the removal. The number of Argentine ants which had gathered to each bait was counted. The number of the spots counted was 15 in the control plot, 20 in the treated plot A and 25 in the treated plot B. The number of Argentine ants which gathered to each bait (average per one paper dish) is shown in Table 1.

TABLE 1

| | The number of Argentine ants (average per paper dish) | | | | |
|---|---|---|---|---|---|
| | The day before the placement | One hour after the placement | The day before the removal (22 days after the placement) | One hour after the removal | Two hours after the removal |
| Control plot | 31.5 | 72.9 | 56.9 | 61.2 | 61.1 |
| Treated plot A | 70.3 | 12.9 | 4.2 | 14.0 | 22.9 |
| Treated plot B | 94.3 | 18.3 | 15.5 | 22.0 | 33.7 |

The density of Argentine ants in the treated plots A and B was higher than that in the control plot, but the number of ants which had gathered just after the placement of pheromone emitting substance decreased to the one-fifth or less of the number of ants on the day before the placement.

Even 22 days after the placement of the behavior-disrupting agents, the number of the ants remained at a low level of the one-fifth or less of the number of ants on the day before the placement of the agents in each of the treated plots. In the control plot, on the other hand, the number of the ants was almost the same as that just after the placement.

The behavior-disrupting agents were removed 23 days after the placement. The number of ants which had gathered at the baits then showed a remarkable increase in the treated plot one hour after the removal. It increased further two hours after the removal. In the control plot, however, there was almost no change in the number of ants which had gathered at the baits.

From these findings, it is evident that the bait searching activities of Argentine ants were restrained severely by the behavior-disrupting agent.

The invention claimed is:

1. A composition comprising from 71 to 500 mg Z-9-hexadecenal as a trail pheromone and at least one of an antioxidant and an ultraviolet absorber, wherein said composition disrupts the marching or foraging behavior of an Argentine ant and is characterized by the absence of a pesticidally active compound.

2. A method of disrupting the marching or foraging behavior of an Argentine ant, comprising a step of emitting a composition comprising Z-9-hexadecenal into an atmosphere of an area to be treated such that the composition disrupts the marching or foraging behavior of Argentine ants in the area to be treated, said composition being characterized by the absence of a pesticidally active compound; wherein said emitting step comprises emitting the composition from at least one vessel holding from 71 to 500 mg of Z-9-hexadecenal and the composition is emitted from 25 to 250 locations per 100 m² of area to be treated.

3. The composition according to claim 1, wherein the composition comprises Z-9-hexadecenal, an antioxidant, and an ultraviolet absorber.

4. The composition according to claim 1, wherein the composition comprises an antioxidant in an amount of 0.1 to 10 weight percent.

5. The composition according to claim 1, wherein the composition comprises an ultraviolet absorber in an amount of 0.01 to 10 weight percent.

6. The method according to claim 2, wherein said emitting step comprises emitting the composition into the atmosphere on or above the ground of the area to be treated.

7. The method according to claim 2, wherein the composition comprises at least one of an antioxidant and an ultraviolet absorber.

* * * * *